United States Patent [19]

Angehrn

[11] Patent Number: 4,689,227

[45] Date of Patent: Aug. 25, 1987

[54] ANTIBACTERIAL COMPOSITION

[75] Inventor: Peter Angehrn, Böckten, Switzerland

[73] Assignee: Hoffmann-La Roche Inc., Nutley, N.J.

[21] Appl. No.: 890,248

[22] Filed: Jul. 24, 1986

Related U.S. Application Data

[63] Continuation-in-part of Ser. No. 695,783, Jan. 28, 1985, abandoned.

[30] Foreign Application Priority Data

Feb. 3, 1984 [CH] Switzerland ............................ 512/84

[51] Int. Cl.$^4$ ............................................. A61K 35/00
[52] U.S. Cl. ..................................................... 424/114
[58] Field of Search .......................................... 424/114

[56] References Cited

FOREIGN PATENT DOCUMENTS 0093376 11/1983 European Pat. Off. ............ 424/114

OTHER PUBLICATIONS

The Merck Index, 10th Ed., 1983, Merck & Co., Inc., Rahway, W. J., pp. 57 and 58.

Primary Examiner—Jerome D. Goldberg
Attorney, Agent, or Firm—Jon S. Saxe; Bernard S. Leon; Richard J. Mazza

[57] ABSTRACT

The antibacterially-active substance composition consisting of mecillinam and (2S,3S)-3-((Z)-2-(2-amino-4-thiazolyl)-2-((carboxymethoxy)imino)acetamido)-2-((carbamoyloxy)methyl-4-oxo-1-azetidinesulphonic acid (compound A), or pro-drugs and/or pharmaceutically usable salts thereof, has a pronounced synergism against Enterobacter strains which are resistant to mecillinam and which are only moderately sensitive to compound A.

12 Claims, No Drawings

ANTIBACTERIAL COMPOSITION

CROSS-REFERENCE TO RELATED APPLICATION

This is a continuation-in-part of application Ser. No. 695,783, filed Jan. 28, 1985, abandoned.

BACKGROUND OF THE INVENTION

1. Field of the Invention

The present invention is concerned with an antibacterially-active pharmaceutical composition consisting of mecillinam and (2S,3S)-3-((Z)-2-(2-amino-4-thiazolyl)-2-[(carboxymethoxy)imino]acetamido)-2-[(carbamoyloxy)-methyl]-4-oxo-1-azetidinesulphonic acid (which is referred to hereinafter as compound A) or pro-drugs and/or pharmaceutically usable salts each of the foregoing compounds. Further, it is concerned with a medicament having synergistic properties based on this composition and with the use of the composition in the prophylaxis and therapy of bacterial infections.

The medicaments in accordance with the invention contain as the active ingredients the amidino-penicillanic acid mecillinam (also known as aminocillin), a pro-drug, for example, the pivaloyloxy methyl ester of mecillinam and/or a pharmaceutically usable salt thereof, in combination with compound A, a pro-drug and/or a pharmaceutically usable salt thereof, as well as therapeutically inert, non-toxic, pharmaceutical carrier materials and, if desired, pharmaceutical adjuvants.

2. Description of the Prior Art

Mecillinam (Amdinocillin) is a known amidinopenicillanic acid having antibacterial activity; see, for example, British Patent Specification No. 1,293,590. Compound A is also a known compound having antibacterial activity; see, for example, European Patent Publication No. 93,376. Further, it is known to combine mecillinam with other antibiotically-active compounds for the purpose of mutually potentiating the two activities; see British Patent Specification No. 2,113,997A.

As is known, strains having inducible, chromosomal-determined β-lactamase can develop very rapidly resistance to a large number of β-lactam antibiotics, including new penicillins and cephalosporins. Genera of micro-organisms which are most adaptive in this connection are Enterobacter and Pseudomonas. Compounds or compositions of compounds having an activity against resistant strains of Enterobacter and/or Pseudomonas are accordingly of extraordinarily high value in the control of bacterial infections caused by these named microorganisms.

DESCRIPTION OF THE INVENTION

In the scope of the present invention it has been ascertained that compound A, which has hitherto not been considered as a combination partner for mecillinam, is especially well suited for such a combination. Compared with already known active substance compositions having the same type of activity, the novel active substance composition in accordance with the present invention exhibits therapeutic advantages which were not foreseeable by a person skilled in the art. Thus, it that been ascertained that the active substance composition in accordance with the invention has a pronounced synergism to Enterobacter strains which are resistant to mecillinam and which are only moderately sensitive to compound A. Because of the pronounced synergism of the novel active substance composition in accordance with the invention, these strains are, however, very sensitive to this composition.

In the following Table there are presented for the composition in accordance with the invention the minimum inhibitory concentrations (MIC values in μ/ml) determined in in vitro comparative tests in the case of various infections with pathogenic microorganisms.

TABLE 1

In vitro activity of compound A and mecillinam (MEC) against various strains of bacteria (MIC μg/ml) Method: Agar dilution test with DST agar (Oxoid)

| | | | Compound A + MEC | | * | |
|---|---|---|---|---|---|---|
| | Compound A | MEC | 1 + 1 | 1 + 4 | | |
| Enterobacter cloacae MK 373 | 4 | >256 | 1 + 1 | 0.25 + 1 | S | S |
| Enterobacter cloacae P99 | 16 | >256 | 2 + 2 | 2 + 8 | S | S |
| Enterobacter cloacae 908 | 32 | >256 | 4 + 4 | 2 + 8 | S | S |
| Enterobacter cloacae 5 | 8 | >256 | 2 + 2 | 2 + 2 | S | S |
| Enterobacter cloacae MK 1617 | 32 | >256 | 4 + 4 | 4 + 16 | S | S |
| Enterobacter cloacae 163 | 32 | >256 | 4 + 4 | 2 + 8 | S | S |
| Enterobacter agglomerans 960 | 16 | >256 | 8 + 8 | 4 + 16 | (S) | S |
| Citrobacter freundii 1982 | 4 | >256 | 4 + 4 | 2 + 8 | — | (S) |
| Citrobacter freundii 1385 b | 8 | >256 | 4 + 4 | 2 + 8 | (S) | S |
| Escherichia coli 5/9 | 2 | >256 | 0.5 + 0.5 | 0.25 + 1 | S | S |
| Acinetobacter anitratus 5I-156 | 16 | >256 | 16 + 16 | 8 + 32 | — | (S) |
| Pseudomonas aeruginosa 1920 E | 4 | >256 | 4 + 4 | 4 + 16 | — | — |
| Pseudomonas aeruginosa 1937 E | 2 | >256 | 2 + 2 | 4 + 16 | — | — |
| Pseudomonas aeruginosa 143724 R | 8 | >256 | 16 + 16 | 16 + 64 | — | — |
| Pseudomonas aeruginosa 5646 | 8 | >256 | 16 + 16 | 16 + 64 | — | — |
| Pseudomonas aeruginosa 5748 | 8 | >256 | 16 + 16 | 8 + 32 | — | — |

*S: Synergism (F.I.C. Index: ≦0.5)
(S): Additive activity (F.I.C. Index: 0.51–1.00)
—: Indifference (F.I.C. Index: 1.01–4.0)
F.I.C. (fractional inhibitory concentrations) Index:

$$\frac{MIC_{compound\ A\ in\ combination}}{MIC_{compound\ A\ alone}} + \frac{MIC_{mecillinam\ in\ combination}}{MIC_{mecillinam\ alone}}$$

(according to G. B. Elion et al, Journal of Biological Chemistry 208: 477–488 [1954])

As mentioned above, the composition in accordance with the invention can contain mecillinam and compound A as such or in the form of salts or of pro-drugs. As suitble salts of the two active substances there come into consideration primarily the alkali metal, alkaline earth metal and ammonium salts. For the formation of ammonium salts there come into consideration bases such as ammonia, triethylamine, pipidine, morpholine, cyclohexylamine, monoethanolamine, diethanolamide, dibenzylethylenediamine, benzyl-β-phenyl-ethylamine, and the like. Mecillinam also forms pharmaceutically usable salts with inorganic and organic acids which usually come into consideration for this purpose, such as hydrochloric acid, sulphuric acid, phosphoric acid, formic acid, acetic acid, succinic acid, lactic acid, citric acid, maleic acid, fumaric acid, tartaric acid, methanesulphonic acid, p-toluenesulphonic acid, and the like.

The term "pro-drug" used in this description embraces any derivative of mecillinam or of compound A which after administrative is converted in the body into mecillinam or into compound A. Examples of such pro-drugs are esters which are hydrolyzable in the body, such as lower alkanoyloxy-lower alkyl and lower alkoxycarbonyloxy-lower alkyl esters of the carboxylic acid groups of mecillinam or of compound A. Again, these esters can be used as such or as pharmaceutically usable salts. Examples of such esters are the pivaloyloxymethyl ester and the methoxy-carbonyloxy-methyl ester.

The residues denoted by "lower" have 1-7, preferably 1-4, carbon atoms. The term "alkyl" denotes straight-chain or branched, saturated hydrocarbon residues such as methyl, ethyl and t-butyl. The term "alkoxy" denotes alkyl groups bonded via an oxygen atom.

The weight ratio of mecillinam to compound A can vary in the compositions and medicaments in accordance with the invention in the range of 1 to 100 to 100 to 1 (1:100 to 100:1), more usually 1 to 64 to 64 to 1 (1:64 to 64:1), and most preferably 1 to 10 to 10 to 1 (1:10 to 10:1).

The manufacture of the medicaments can be carried out in a manner which is familiar to any person skilled in the art by mixing the two active substances with suitable, non-toxic, inert, therapeutically compatible solid or liquid carrier materials, including the usual adjuvants such as stabilizing agents, preserving agents, wetting agents, emulsifying agents, flavour-improving agents, salts for varying the osmotic pressure or buffer substances.

The administration can be carried out parenterally or orally. In human medicine the daily dosage lies between about 100 mg and about 5 g of the composition. The daily dosage is conveniently administered in several dosage units, for example, twice to 5 times daily with 50–1000 mg of the active substance composition being administered each time. Accordingly, the medicaments used in human medicine conveniently contain 50 to 1000 mg of the active substance composition.

In an alternate embodiment, a conventional unit dosage form of mecillinam or a pro-drug or salts thereof can be administered concurrently (at the same time or about the same time) with a conventional unit dosage form of Compound A or pro-drugs and/or pharmaceutically acceptable salts thereof to treat warm blooded animals having bacterial infections. The weight ratios set out above are the same in which mecillinam and Compound A can vary, for example, 1 to 100 to 100 to 1, more usually 1 to 64 to 64 to 1, and most preferably 1 to 10 to 10 to 1, when administered concurrently in unit dosage form.

Both dosage unit forms can each be administered parenterally or orally, for example, pivmecillinam (orally)—Compound A in injectable form.

In human medicine, the daily dose of each component lies between 50 mg and 2.5 g to provide, as indicated above, between about 100 mg to about 5 g of the two components when administered concurrently. The daily dosage is conveniently administered in several dosage units, for example, twice to 5 times daily with 25–500 mg of each one of the active substances being administered each time. The medicaments when used concurrently in human medicine conveniently provide 50 to 1000 mg of the combination of the active substances to the subject being treated for bacterial infection as when a composition of the two is utilized.

DESCRIPTION OF THE SPECIFIC EMBODIMENTS

The following Examples illustrate the manufacture of suitable dosage forms.

EXAMPLE 1

Ampoule vials are manufactured in a manner known per se, each ampoule vial containing:

| | |
|---|---|
| Mecillinam | 500 mg |
| Monosodium salt of compound A | 500 mg |
| Total | 1000 mg |

The two components are sieved through a 0.3 mm sieve and mixed well with one another. The powder obtained is filled into 20 ml ampoule vials, which are then sealed. In order to prepare an injection solution, the content of one ampoule vial is dissolved in 8 to 10 ml of water before use.

EXAMPLE 2

Tablets are manufactured in a manner known per se, each tablet containing:

| | |
|---|---|
| Pivmecillinam hydrochloride | 100 mg |
| Compound A | 400 mg |
| 1-Vinyl-2-pyrolidinone polymer | 3 mg |
| Isopropanol | 0.05 mg |
| Magnesium stearate | 5 mg |

The pivmecillinam hydrochloride (pivaloyloxymethyl ester of mecillinam hydrochloride) is granulated with a solution of the 1-vinyl-2-pyrolidinone polymer in isopropanol. The granulate is dried at 40° C., sieved through a 0.7 mm sieve and mixed well with compound A and the magnesium stearate. The mixture is pressed on a tabletting machine into tablets having a diameter of 12 mm and a weight of 560 mg.

EXAMPLE 3

Capsules are manufactured in a manner known per se, each capsule containing:

| | |
|---|---|
| Mecillinam | 200 mg |
| Compound A | 200 mg |
| Magnesium stearate | 4 mg |
| Total | 404 mg |

The substances are sieved through at 0.6 mm sieve and mixed well with one another. The powder mixture obtained is filled into gelatine capsules No. 0.

EXAMPLE 4

Preparations for intramammary injection are manufactured in a manner known per se, each injection syringe containing:

| | | |
|---|---|---|
| Mecillinam | | 150 mg |
| Monosodium salt of compound A | | 150 mg |
| Aluminium monostearate | | 100 mg |
| 12-Hydroxystearin | | 100 mg |
| Liquid paraffin | | 4500 mg |
| | Total | 5000 mg |

The aluminium monostearate and the 12-hydroxystearin are dissolved in the liquid paraffin at 130° C. and cooled to 30° C. The mecillinam and the monosodium salt of compound A are ground into particles below 50 micron and thereafter dispersed in the intramammary base. After homogenization using a colloid mill, the intramammary preparation is filled into plastic injection syringes.

EXAMPLE 5

Sachets of the following composition are manufactured in a manner known per se:

| | |
|---|---|
| Mecillinam | 3000 g |
| Monosodium salt of compound A | 1500 g |
| Sucrose | 30000 g |
| Sodium citrate | 250 g |
| Sodium carboxymethylcellulose | 250 g |
| Peppermint flavour | 10 g |

The components are sieved through a sieve of 0.5 mm, mixed and filled into sachets containing 3.5 g of the mixture. The content of one sachet is dissolved in approximately 10 ml of water before use.

I claim:

1. A composition comprising mecillinam and (2S,3S)-3-[(Z)-2-(2-amino-4-thiazolyl)-2-[(carboxymethoxy)imino]acetamido]-2-[(carbamoyloxy)methyl]-4-oxo-1-azetidine sulphonic acid, or a pharmaceutically acceptable ester of either of the foregoing which is hydrolyzable in the body to form the compound, or a pharmaceutically usable salt of either of the foregoing, wherein the weight ratio of these two ingredients respectively is from 1:16 to 64:1.

2. A composition as in claim 1, wherein the hydrolyzable ester of mecillinam is pivmecillinam.

3. A composition in accordance with claim 1, wherein the weight ratio of the two ingredients is from 1 to 10 to 10 to 1.

4. A composition according to claim 1, wherein the hydrolyzable ester is a member of the group consisting of lower alkanoyloxy-lower alkyl and lower alkoxycarbonyloxy-lower alkyl esters of the carboxylic acid groups of said ingredients.

5. A medicament containing the composition of claim 1 and a therapeutically inert carrier material.

6. A medicament in accordance with claim 5, which contains 50–1000 mg of the composition.

7. A method of treating bacterial infection in a warm-blooded animal, comprising administering to the animal a bacteriostatically effective amount of a composition comprising mecillinam and (2S,3S)-3-[(Z)-2-(2-amino-4-thiazolyl)-2-[(carboxymethoxy)imino]acetamido]-2-[(carbamoyloxy)methyl]-4-oxo-1-azetidine sulphonic acid or a pharmaceutically acceptable ester of either of the foregoing which is hydrolyzable in the body to form the compound, or a pharmaceutically usable salt of either of the foregoing, wherein the weight ratio of these two ingredients respectively is from 1:16 to 64:1.

8. A method as in claim 7, wherein the hydrolyzable ester of mecillinam is pivmecillinam.

9. A method in accordance with claim 7, wherein the weight ratio of the two ingredients in from 1 to 10 to 10 to 1.

10. A method in accordance with claim 7, wherein the hydrolyzable ester is a member of the group consisting of lower alkanoyloxy-lower alkyl and lower alkoxycarbonyloxy-lower alkyl esters of the carboxylic acid groups of said ingredients.

11. A method in accordance with claim 7, in which the composition is used in a medicament which contains a therapeutically inert carrier material.

12. A method in accordance with claim 11, in which the medicament contains 50–1000 mg of the composition.

* * * * *